United States Patent [19]

Cox, Jr. et al.

[11] 3,983,399
[45] Sept. 28, 1976

[54] TOMOGRAPHY SYSTEM HAVING AXIAL SCANNING

[75] Inventors: Jerome R. Cox, Jr., St. Louis; Donald L. Snyder, Clayton, both of Mo.

[73] Assignee: Picker Corporation, Cleveland, Ohio

[22] Filed: Mar. 18, 1975

[21] Appl. No.: 559,412

[52] U.S. Cl. .......................... 250/445 T; 250/449; 250/362; 250/363 S; 250/490
[51] Int. Cl.² ..................................... G01M 23/00
[58] Field of Search ............... 250/445 T, 449, 362, 250/363, 490, 491, 402, 416

[56] References Cited
UNITED STATES PATENTS

| | | | |
|---|---|---|---|
| 3,106,640 | 10/1963 | Oldendorf | 250/360 |
| 3,158,744 | 11/1964 | Bernstein | 250/360 |
| 3,432,657 | 3/1969 | Slavin | 250/359 |
| 3,778,614 | 12/1975 | Hounsfield | 250/362 |
| 3,866,047 | 2/1975 | Hounsfield | 250/360 |

OTHER PUBLICATIONS

"Cylindrical and Section Radioisotope Scanning of the Liver and Brain" Kuhl et al., Radiology, vol. 83, No. 5, pp. 926–936, 1964.

*Primary Examiner*—Alfred E. Smith
*Assistant Examiner*—B. C. Anderson
*Attorney, Agent, or Firm*—Watts, Hoffmann, Fisher & Heinke Co.

[57] ABSTRACT

An improved method and apparatus for transaxial tomographic scanning a patient. A scanning system is provided having a rotatably mounted X-ray radiation source/detector assembly which orbits and scans the patient in a plane of orbit. The source provides a plurality of beams of radiation having axes in the orbital plane. The beams pass through the patient to an array of detectors each of which is and respectively aligned with a different one of the beams. Radiation intensity data is collected at predetermined orientation of each beam - detector pair as the assembly orbits about the patient. In one embodiment the source and detector are rotated as a unit through a rotation angle $\phi$ about center of rotation while the assembly orbits the patient through an orbit angle $\gamma$. Measurements are taken as the beams from the X-ray source sweep, due to the source detector rotation relative to a patient, through substantially uniformly spaced, coplanar points $[t, (k), \theta(n)]$ defined from an origin lying in the plane of orbit. Exact reconstruction is achieved when measurements are taken at the angles $\phi$, $\gamma$ characterized substantially as $$\phi = \sin^{-1} [k \, \Delta \, t/d] \text{ and } \gamma = \phi + n \, \Delta \, \theta,$$

where $d$ represents the distance between the origin and the center of rotation, and $k$, $n$ are integers.

14 Claims, 21 Drawing Figures

TOMOGRAPHY SYSTEM HAVING AXIAL SCANNING

References to Relevant and Related Patents and Applications

U.S. Pat. No. 3,803,415, issued Apr. 9, 1974, entitled METHOD AND APPARATUS FOR INSPECTING TIRES WITH X-RAY (here the X-RAY patent);

U.S. Pat. application Ser. No. 301,529 filed on Oct. 27, 1972, entitled METHOD AND APPARATUS FOR INSPECTING TIRES (here the "METHOD" patent application);

U.S. Pat. application Ser. No. 95,859, filed Dec. 7, 1970, entitled TIRE INSPECTION APPARATUS (here the APPARATUS patent application);

This application is based on Disclosure Document No. 017790, entitled, "X-ray Absorption Density by Compound Scanning," filed Mar. 19, 1973.

BACKGROUND OF THE INVENTION

This invention relates generally to the examination of a patient by means of radiation and, more particularly, to method and apparatus for tomographically examining an internal section of a patient by scanning a beam of X-radiation from a radiation source as the source orbits the patient.

Field of the Invention

A conventional radiograph is a two-dimensional shadow image of a three-dimensional object. The depth dimension is not apparent as all interior portions of the object appear to be in a single plane. As a consequence a conventional radiograph fails to provide detail as to three-dimensional spatial location of a condition. Under some conditions a conventional radiograph is difficult to interpret and it may not reveal a condition which exists.

The science of tomography developed which examined cross-sectional planes of a patient by sequentially bombarding the patient with X-rays from a plurality of directions. Conventional tomographic systems utilized a radiation sensitive recording film plate whose movement was coordinated with movement of a radiation source. The source-recording plate pair moved about a system axis passing through the patient and recorded a cross-sectional image of the patient in a plane which was transverse to the axis of the X-ray beam. The movement of the source-recording plate pair was such that elements in the selected cross-sectional plane of the patient were continuously scanned by the beam. This scanning technique resulted in movement on the film of images of the elements out of the selected plane, and these images were blurred with the result that an image of the selected plane was produced.

Conventional tomographic techniques resulted in loss of information, as elements in the other planes cast shadows in the selected cross-sectional plane of the patient. These shadows reduce the quality of the image recorded on the X-ray film as compared with transaxial techniques used in the present invention.

Prior Art

Variations were developed in forming the image which resulted from conventional tomographic scanning techniques. According to one proposal, the recording plate was to be replaced with a radiation sensitive detector which orbited in aligned synchronism with the radiation source. More specifically, the source/detector pair was to be angularly rotated in a plane as the beam of radiation passed through the patient. The patient and source were to be periodically translated relatively in the plane of rotation and the rotation was then repeated. The angular rotation was to be about a system axis which passed through the patient, and the beam of radiation passed through the system axis. By passing the beam through the system axis as the source was to be rotated, a small central region within the patient could be isolated by cancelling the affects of all areas remote from the central region. Translation of the patient would allow an image of a section of the patient in the plane of rotation to be reconstructed as a video image displaying an integration of information from a series of small central areas. Tomography which produces an image in a plane which includes the X-ray beam axis is known as transverse section tomography.

Another proposal suggested the use of a plurality of radiation detectors disposed in a line in the direction of patient translation in an attempt to increase the effective allowable translation speed. Even with the multiple detectors, these proposals using an orbital scan motion coupled with a linear translation motion resulted in a system requiring long scanning times to provide images of limited size and quality.

A type of scanning system is described in Kuhl, et al., "Transmission Scanning, A Useful Adjunct to Conventional Emission Scanning For Accurately Keying Isotope Deposition To Radiographic Anatomy," Radiology, 1966, Vol. 87, pp. 278–284. The referenced "Emission" scanning system uses a detector for scanning a patient who has had radioisotope administered. The detector measures intensity values of the radiation as it is emitted. Transmission scanning differs from emission scanning in that it uses a radiation source to transmit a beam of radiation through the patient instead of radiation from an administered radioisotope. An emission scanning tomographic system is described in D. E. Kuhl and R. Q. Edwards, "Cylindrical and Section Radioisotope Scanning of the Liver and Brain," Radiology, Vol. 83, No. 5, pp. 926–936; 1964.

The science of reconstruction tomography using transverse section scanning has evolved to a system where a radiation source/ detector pair scans a patient with a beam of radiation emitted as the source detector/pair are translated with the beam axis in a plane containing the section of the patient to be examined. The angular orientation of the beam is changed from one scan to another. The detected intensity of the beam is recorded for computing X-ray transmission or X-ray absorption characteristics through the scanned section. A plot of these characteristics provides a reliable image of the internal structure of the patient in the scanned plane. Transverse section scanning is also described in the above Kuhl, et al., references.

In one proposed reconstruction tomographic system using transverse section scanning, a linearly disposed array of source/ detector pairs were to rectilinearly scan a patient along a path at a first angle with respect to an axis passing through the patient. Radiation intensity values were to be recorded during the rectilinear scan. After completing a rectilinear scan of the patient at the first angle the source/detector pair were to be angularly indexed. A second rectilinear scan was to be performed on the patient along a second path at a second angle with respect to the axis, and so forth.

After rectilinearly scanning along paths covering 180° of angles with respect to the axis, the intensity data collected from radiation measurements were processed utilizing a method of successive approximations. A reconstructed image was generated representing the X-ray transmission or X-ray absorption coefficients lying in a section of the patient.

Apparatus for performing the rectilinear scans, was massive and required undue motive forces for linearly accelerating, decelerating and reversing direction of the array of the source-detector pair. This is better appreciated when understanding that, for a complete study, 180 scans were required. A complete study thus required 180 translational and 180 rotational accelerations and decelerations, as well as 180 direction changes during translation. In addition, the large number of accelerations, decelerations and direction changes resulted in a system requiring an undue amount of scanning time. A minimum scanning time is essential to minimize the time required for completing a study to thus protect the patient from excessive amounts of radiation and minimize the effects of changing conditions in the patient.

A prior proposal has suggested the transverse section scanning of a specimen by a source/detector pair which orbited about an orbiting system axis which passed through the patient. The system axis was slowly orbited to trace a circle of small diameter as the source-detector pair orbited about the system axis. The proposal failed to disclose how to implement a system which provided the required circular motion on the system axis. Apparatus for revolving the source/detector pair in such a proposal is subjected to extreme inertial forces due to the mass of the source/detector pair. Practicality required that the system axis be stationary if the source/detector pair is to be revolved with the precision required for exact image reconstruction. Furthermore, the proposal failed to disclose the relationships among the rotation about the system axis, the optimum angles of radiation measurement, the speed of orbit about the system axis, and the speed of rotation of the system axis in the circular motion.

The prior art has also suggested a transverse section, transmission scanning system which would orbit a source-detector pair about a system axis which passed through the patient. Concurrently with the orbiting the source-detector pair were to be rotated in the plane of the orbit about an orbiting source axis which passed through the source and which orbited about the system axis. The use of an array of detectors disposed symmetrically of the plane of orbit was also suggested. The proposal failed to disclose the relationships among the rotation of the system axis, the rotation of the source axis, and the orientations of the source/detectors at which measurements were to be taken if exact reconstruction was to be achieved. The reference also failed to disclose apparatus for implementing the suggested system. Furthermore, the suggestion did not recognize that data collected by this dual axial motion was not in the sequence required by the reconstruction algorithm disclosed with this suggestion. Without this recognition and a suggestion as to the solution of this problem, data collected by this scanning motion would not provide clinically acceptable results.

SUMMARY OF THE INVENTION

The above noted and other deficiencies are overcome by the present invention in providing a transverse section, reconstruction tomographic system which scans a patient with an orbiting radiation source-detector assembly. A beam of radiation is scanned over paths which render exact reconstruction and which minimize the number of required reversals in the direction of scan motion and in the number of required accelerations and decelerations of the source-detector assembly. By reducing the number of accelerations, decelerations, and direction reversals, the invention minimizes the amount of time required for completing a study.

The reconstruction tomographic system scans a beam of X-radiation through an interior section of the patient. The intensity of the beam is measured for determining X-ray absorption or transmission coefficients within the interior section of the patient. An image is then reconstructed from the X-ray transmission or absorption coefficient at coplanar points $[t_k, \theta_n]$ about an origin in the plane containing the section.

A radiation source-detector assembly is rotatably mounted and supported for orbit about the origin and in the section plane. One or more collimated beams of radiation of relatively small cross-sectional area are transmitted from the source through the patient to one or more aligned detectors. Data collection apparatus, including the radiation detector, measure intensity values of the beams at an array of measurement points defined by an angle $\phi$ of rotation and an angle $\gamma$ of orbit characterized substantially as $\phi = \sin^{-1}(k \Delta t/d)$ and $\gamma = \phi + n \Delta \theta$, where $d$ represents the distance between the origin and the center of rotation of the rotatable source detector pair, and $k$ and $n$ are integers.

A generally C-shaped support apparatus having a pair of arms is provided and is rotatable about a centrally located pivot. The source-detector assembly is mounted to rotate about a source axis through one of the arms of the support apparatus (thereby defining the angle $\phi$). Rotation of the support apparatus causes the source-detector assembly to orbit about the pivot (thereby defining the angle $\gamma$). As the support apparatus rotates about the pivot, each beam from the source-detector assembly traces a scanning path which encompasses measurement points of the array. The rotary and orbital motions are controlled and synchronized to enable exact reconstruction of an image representing the X-ray absorption or transmission coefficients of the interior sections of the patient.

It is accordingly an object of the present invention to provide an improved method and apparatus for tomographically scanning a patient with an orbiting radiation source-detector pair which provides exact image reconstructions in a minimal amount of scanning time and with a minimum number of accelerations and decelerations of the pair.

DETAILED DESCRIPTION OF A PREFERRED EMBODIMENT

Figure 1:
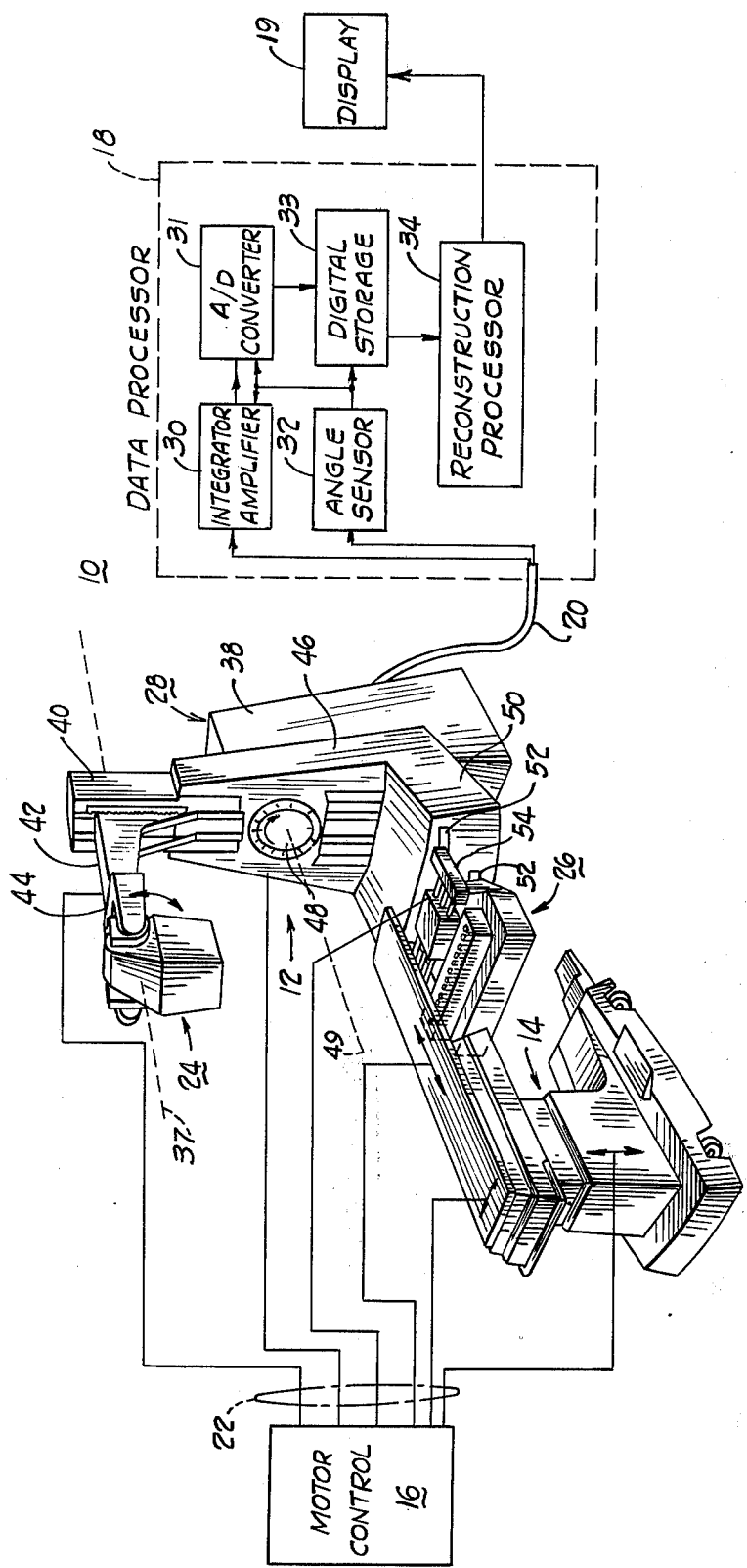
FIG. 1 is a combined perspective and functional representation of a reconstruction tomographic system having scanning apparatus according to this invention.

Referring to FIGS. 1 – 5 a transverse section, reconstruction tomographic system is shown generally at 10. The tomographic system 10 includes scanning apparatus 12, a patient supporting stretcher 14, a motor controller 16, a data processor 18 and a display 19. The scanning apparatus 12 is operable in response to the controller 16 for X-ray scanning a transverse section of a patient (not shown) on the stretcher 14 from a multiplicity of coplanar angles. The scanning apparatus 12 derives radiation intensity data from collimated beams of X-rays after they pass through the section of patient. The collected data is coupled by a data cable line 20 to the data processor 18. The data processor 18 reconstructs an image of the internal section of the patient by computing the coefficients of X-ray absorption or transmission. The reconstructed image is provided by a plot of the coefficients on the display 19.

The stretcher 14 movably supports the patient in position for examination near the scanning apparatus 12. The stretcher 14 is mounted on wheels and is motor driven in response to signals on a set of lines 22 from the controller 16 for elevating and translating the patient into position.

The scanning apparatus 12 comprises a radiation source assembly 24, a radiation detector assembly 26, and support structure 28 which supports the source and detector assemblies 24, 26 diametrically about the patient. The radiation source assembly 24 provides a plurality of collimated, coplanar beams of X-radiation to the radiation detector assembly 26. The radiation detector assembly 26 has a radiation detector aligned for receiving each beam from the source assembly 24. Each radiation detector generates output signals indicative of the intensity of the respective X-ray beam after it has passed through the patient.

The support structure 28 is rotated through a sequence of arcs at least 180° or continuously through 360° at speeds up to 15 rpm under control of the motor controller 16 via the lines 22. Rotation of the support structure 28 provides relative motion between a patient on the stretcher 14 and the beams of radiation from the source assembly 24 which pass through the patient. The support structure 28 holds the radiation detector assembly 26 in alignment with the radiation source assembly 24 for maintaining reception of the beams of radiation by the detector assembly 26.

The support structure 28 comprises a C-shaped yoke member 36 pivotally mounted on a stationary support pedestal 38. The source assembly 24 and the detector assembly 26 are each rotatably mounted to the yoke member 36. The C-shaped yoke member 36 defines a source axis 37 rotatably supports the radiation source assembly 24 and the radiation detector assembly 26 in relatively fixed alignment. Rotation of the C-shaped yoke member 36 effects orbiting of the radiation source assembly 24 and the radiation detector assembly 26 about the patient in a fixed plane.

The assemblies 24, 26 rotate about the yoke member 36 via a motor drive. The motor drive rotates the assemblies about the yoke member at a speed of 20° of arc per second within the plane of orbit. Rotation of only one degree suffices for a high level of resolution when the assemblies 24, 26 scan with a plurality of coplanar beams. If only a single beam is scanned through the patient, it is understood that the assemblies 24, 26 would rotate through a greater angle. The necessary modification to the yoke member 36 to accommodate the greater angle of rotation is obvious.

The assemblies 24, 26 are rotated about the C-shaped yoke member 36 and the yoke member 36 is rotated about the pivot by stepping motors which are under the control of the motor controller 16. The motor controller 16 comprises conventional circuits for controlling the operation of stepping motors and for providing encoded data representative of the angular position of the output shafts of the stepping motors. Any of a variety of thyristor motor starter and stepping relay control circuits could be utilized by one of ordinary skill to power the scanning apparatus 12 according to this invention. Similarly, any of a variety of digital shaft encoders, preferably of the absolute type, are suitable for coupling to motors in the apparatus 12 for defining absolute angular position of the respective output shafts of the motors. The absolute angular position of each respective output shaft is directly indicative of the amount of rotation caused by the motor.

The data processor 18 is responsive to the output signals from the radiation detector assembly 26 and to the encoded position data from the shaft encoders for providing a reconstructed image representative of the absorption coefficients in the section of the patient lying in the plane of the source-detector orbit. The processor 18 may be conventional data processing circuitry utilized in the X-ray transmission scanning technology and will only be described briefly.

The processor 18 comprises a charge integrator/amplifier 30, an analog-to-digital converter 31, an angle sensor 32, a digital storage circuit 33, and a reconstruction processor 34.

The period of time over which the data signals are averaged is determined according to start and stop signals generated by the angle sensor 32, or to a period determined by the speed of rotation of the assemblies 24, 26. The integrator amplifier 30 is responsive to the output signals from the radiation detector assembly 26 for providing averaged, analog data signals. These data signals have values representing the intensity of the X-ray beam after it has passed through and been attenuated by the patient. The A/D converter 31 is responsive to the averaged, analog signals and converts them to digital signals. The digital storage 33, is preferably a memory of a digital computer and retrievably stores the digital signals in coordination with the angle sensor 32. More specifically, the angle sensor 32 is responsive to the digital shaft encoders in the motor controller 16 and provides orientation signals indicative of the orientations of the assemblies 24, 26. Values of the orientation signals are compared with a store of predetermined values representing orientations at which measurements are to be taken. In response to the comparison of the sensed values with the stored values, the digital computer either controls the location in which the digital signals are stored or it labels each location in which the digital signals are stored. The digital computer comprising the reconstruction processor 34 is programmed for tomographic reconstruction using any of a variety of known computational processes. Well known computational processes include techniques using filtered back projections, matrix multiplication, and successive approximations. Reconstruction provides values which, when plotted and displayed, represent radiation absorption or transmission coefficients of the section of the patient scanned. More specifically, the digital signals corresponding to values of absorption at preselected angles of orbit and rotation of the source-detector assemblies 24, 26 are retrieved from the storage 33. These values are processed by the reconstruction processor 34 and are plotted as points of the reconstructed image which is displayed on the display 19.

Referring to the C-shaped yoke member 36 in more detail, it includes an upper support member 40 and a lower support member 46. The lower support member 46 is rotatably mounted to the stationary support member 38 on a shaft 48. The lower support member 46 is configured in the shape of an L which is swept through an arc forming an arcuate shaped ledge portion 50. The ledge portion 50 has arcuate shaped slots 52 through which the detector assembly 26 is movably mounted via a detector mounting assembly 54.

The upper support member 40 has an arm 42 coupled to a rotatable pivot bracket 44. The pivot bracket 44 is coupled via a source mounting assembly 45 to the radiation source assembly 24. The pivot bracket 44 enables the source assembly 24 to rotate about the arm 42 through an angle $\phi$ (hereafter referred to as the rotational angle $\phi$) in the plane of the orbit. When a plurality of coplanar beams are used for scanning, the rotational angle $\phi$ is measured from the center of the span of the beams, and the value incorporates the angle subtended by the array. For example, a value of the angle $\phi$ equal to 20° is implemented by a plurality of nonsweeping beams spanning the 20°. Alternatively, a single beam sweeping through 20° about the arm 42 sweeps an angle $\phi$ of 20°.

The support structure 28 has a plurality of motors for providing the diverse movements of the source assembly 24 and the detector assembly 26. A support rotating motor 60, a detector assembly rotating motor 62, and a pivot holder rotating motor 64, are provided and are actuated in response to the motor controller 16. Although not shown, it is understood that the plurality of motors are powered through slip-ring connectors between each motor and the lines 22. Because the slip-ring connectors are conventional and do not form a part of the invention, they will not be described in further detail.

Figure 2:
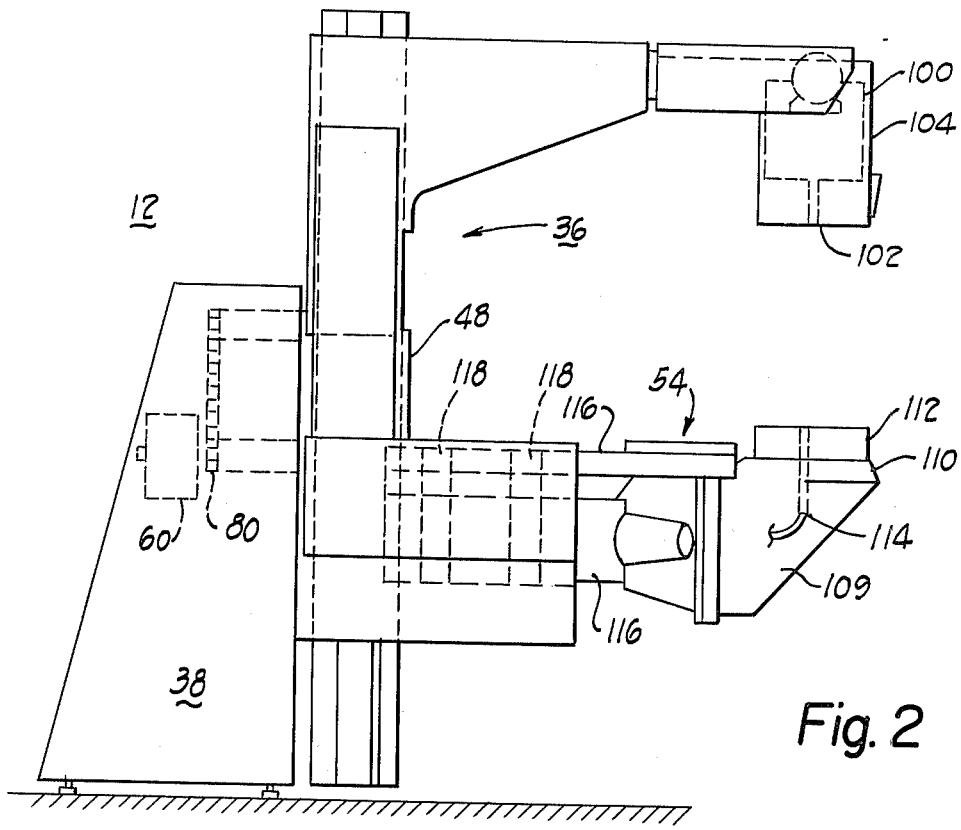
FIG. 2 is a side elevational view of the scanning apparatus on an enlarged scale with respect to FIG. 1.

The support rotating motor 60 is shown in FIG. 2 and is coupled via linkage 80 to the C-shaped yoke member 36. Actuation of the motor 60 rotates the yoke member 36 about the pivot shaft 48 through an angle $\gamma$. The rotation of the C-shaped yoke member 36 effectuates orbiting of the source-detector assemblies 24, 26 through the angle $\gamma$ (hereafter referred to as the orbit angle $\gamma$) about a system axis 49 effectively passing through the pivot shaft 48.

Figure 5:
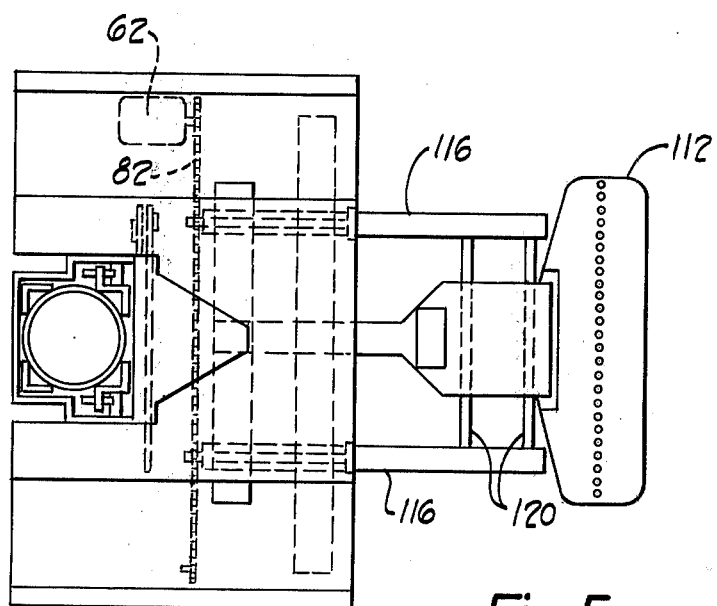
FIG. 5 is a sectional view of the yoke and a plan view of the detector.

The detector assembly rotating motor 62 is shown in FIG. 5 and drives the detector mounting assembly 54 via chain linkage 82. Actuation of the detector assembly rotating motor 62 causes the radiation detection assembly 26 to move in an arcuate path having a center of rotation at the pivot bracket 44.

Figure 3:
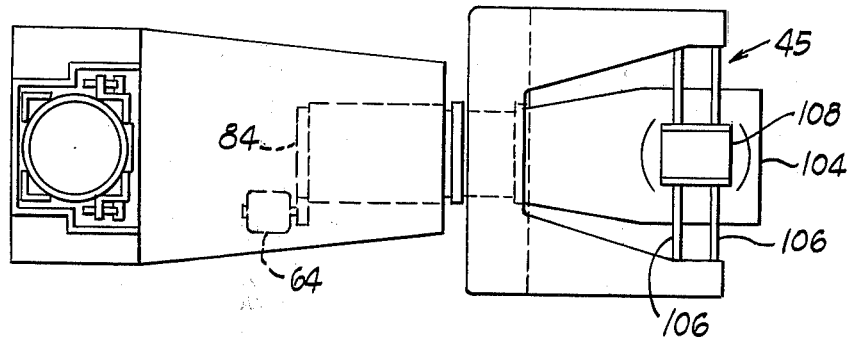
FIG. 3 is a plan view of the yoke and source and detector assemblies.
Figure 4:
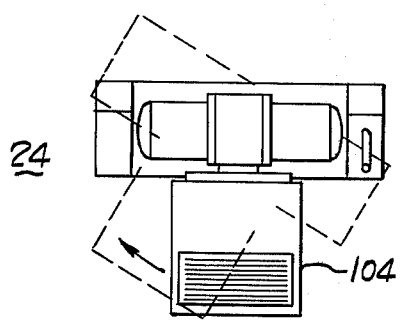
FIG. 4 is a front elevational view of the source.

The pivot rotating motor 64 is shown in FIG. 3 and drives the pivot holder 44 via gear linkage 84. Energization of the pivot bracket rotation motor 64 is synchronized with the energization of the detector assembly rotating motor 62 to maintain alignment of the radiation source assembly 24 and the radiation detector assembly 26.

The radiation source assembly 24 and the source mounting assemby 45 are shown in FIGS. 2 and 3. A source of X-rays, such as a 120kv X-ray tube 100, is provided in cooperation with a source collimator assembly 102 is a housing 104. The X-ray tube has a target which provides a conventional cone-shaped emission of radiation. The collimator assembly 102 delineates a plurality of discrete beams which are directed toward the detector assembly 26. In a preferred embodiment, the collimator assembly 102 provides twenty collimated beams at angle of separation (hereafter referred to as the angle $\alpha$) between adjacent beams of 1°. Each beam is collimated to a width of 0.2° which produces a beam on the order of 2–3 mm. The collimator and the tube target are spaced so that the beams are delineated to approach truly collimated electromagnetic radiation.

The X-ray tube 100 and its associated cooling jacket and plumbing are only shown functionally as they are conventional. Similarly the electrical connections to the tube 100 are not shown as they are conventional and do not form a part of the invention. Suitable X-ray tube assemblies, including the cooling jacket and electrical interconnects, which allow unhindered rotary motion of the X-ray tube as above described are well known, especially in the X-ray tire inspection art. Such assemblies are described in the METHOD and APPARATUS patent applications and in the X-RAY patent, which are incorporated by reference.

The source mounting assembly 45 has a pair of support rods 106. The support rods 106 are journaled into the pivot bracket 44 for supporting the radiation source assembly 24.

The radiation detector assembly 26 is shown in FIG. 2 and includes a housing 109 which is coupled by the detector mounting assembly 54 to the lower support member 46 through the slots 52. The housing 109 encloses a collimator assembly 112 and sets of scintillation crystals 110, and photomultiplier tubes 114. Each scintillation crystal 110 is preferably a thallium activated sodium iodide crystal and is interposed between the detector collimator assembly 112 and a corresponding photomuliplier tube 114. The beams of X-radiation from the source assembly 24 impinge upon the scintillation crystal 110, and scintillations are generated in response to the beams. The scintillations are detected by the photomultiplier tubes 114 which provide electrical output signals representative of the amount of X-radiation received by the scintillation crystal 110. The described radiation detector assembly 26 is conventional in the X-ray scanning art.

The collimator assembly 112 comprises a number of collimator passages corresponding to the number of passages in the source collimator assembly 102. For the preferred embodiment which utilizes twenty beams of radiation, twenty passages are provided in the collimator assembly 112. Axes of adjacent passages are spaced by the angle α of 1° in accordance with the separation of the passages of the source collimator assembly 102. It has been discovered that a 1° spacing between collimator passages satisfactorily reduces the effect of scatter to an acceptable level.

The detector mounting assembly 54 supports the detector assembly 26 for arcuate movement about the pivot bracket 44. It comprises a set of brackets 116, and a plurality of support rods 120. The support rods 120 are journaled into the brackets 116 and support the detector assembly 26. The brackets 116 extend through the slots 52 and are coupled to the chain linkage 82. A pair of guides 118 are provided in the lower support member 46 through which the brackets 116 extend. The guides 118 cause the detector assembly 26 to move in the arcuate path in response to the detector rotating motor 62.

Theory of Operation

Reconstruction tomography commonly utilizes a back projection computational process technique for processing the radiation intensity data to reconstruct the image. The detected and stored value of the X-ray transmission intensity through the patient is projected back in the storage along a path corresponding to the path of the beam that produced the measured value of radiation. The values of radiation transmission measured during each scan are back projected for a scan-by-scan build up of the image. More specifically, each value of the radiation transmission as it is projected back is kept constant, and the respective values of each back projection at all points of intersection are respectively added together. This technique is described in Kuhl, A Clinical Radioisotope Scanner For Cylindrical And Section Scanning, PROC. SYMP., Athens 1964, Medical Radioisotope Scanning, I.A.E.A., Vienna, 1, 273, 1964.

The back projection technique has been improved with the introduction of filtered back projections derived from a theoretical approach utilizing Fourier analysis. A formula for realizing Fourier reconstruction using filtered back projections for emission scanning is set forth in Chesler, THREE-DIMENSIONAL RECONSTRUCTION TECHNIQUE, J. Nucl. Med., 1974.

The method of using filtered back projections to reconstruct a tomographic image is based on Equation 1 below. This equation is similar to that found in Sweeney, *Interferometric Measurement of Three Dimensional Temperature*, PhD Thesis, University of Michigan; 1972.

$$a(x,y) = (\pi/N_\theta) \sum_{n=1}^{N_\theta} f(x \cos \theta_n + y \sin \theta_n; \theta_n), \quad \text{EQN (1)}$$

where i. a $(x,y)$ is the reconstructed, or estimated, value of the desired absorption density at the point $(x,y)$. The estimate is to be evaluated at a discrete set of points $(x_1,y_1), (x_2,y_2), \ldots$ in the $(x,y)$ plane.

ii. $f(x \cos \theta + y \sin \theta; \theta) = f(t;\theta)$ which is a polar coordinate function of the translation variable $t$ determined from the measurements $m(t,\theta)$ at an angle $\theta$ lying within a plane passing through the patient according to $$f(t,\theta) = \int_{-\infty}^{\infty} h(t-\tau)m(\tau,\theta)\, d\tau, \quad \text{EQN(2)}$$

where where $h(t)$ is the filter impulse-response required for reconstructive tomography.

iii. $N$ is the number of angles at which data are collected, where $\theta_n = \pi n/N_\theta$ for $n = 0, 1, \ldots, (N_\theta - 1)$.

In practice, the continuous sum or integral in (2) is replaced by a discrete sum of the form $$f(t;\theta) = \sum_{k=1}^{N_t} h(t-\tau_k)m(\tau_k, \theta)\Delta\tau, \quad \text{EQN (3)}$$

where $N_t$ is the number of translation positions where measurements are made. Solution of the Equation 2 using Equation 3 is readily implemented using the system 10, a digital computer, and the computational process disclosed in the Sweeney publication.

Detailed descriptions of and comparisons of the various computational processes are found in Cho, *Generalized Views on 3-D Image Reconstruction and Computerized Transverse Axial Tomography*, IEEE Transactions on Nuclear Science, Vol. NS-21, June, 1974.

The significance of the compound axial scanning movements of the system 10 for generating $f(t,\theta)$ is best understood when considering FIGS. 6–11. FIG. 6a illustrates a hypothetical cross-section 150 of a patient under study. Its interior points are denoted in polar coordinates as $(t_k, \theta_n)$ about an origin 160 lying within the plane of the cross-section.

Figure 6B:
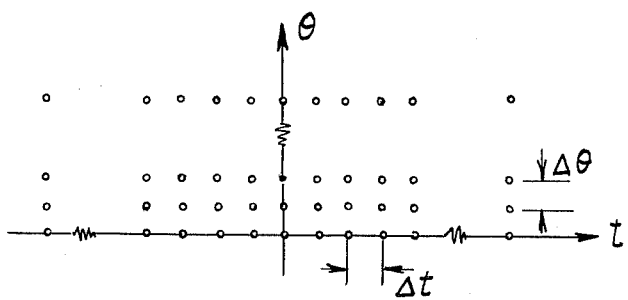
FIG. 6b is a plot of the measurement points in the coordinate system of FIG. 6a which are required for exact image reconstruction.
Figure 6A:
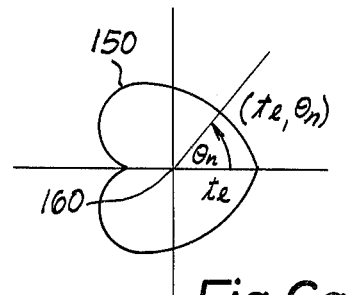
FIG. 6a is a diagrammatic presentation polar coordinate system about an origin lying in a cross-sectional plane of the patient.

FIG. 6b depicts a set of measurement points $m(t_k, \theta_n)$ substantially uniformly spaced in the $(\theta, t)$ plane. Radiation intensity measurements taken at these points, or sufficiently near these points to render accurate interpolations provide exact reconstruction of the cross-section lying in the $(\theta, t)$ plane.

For measurements that are spaced uniformly in the $(\theta, t)$ coordinate system at points indexed by $k$ and $n$ $$t(k) = k(\Delta t), k \in \left\{ \frac{t_{min}}{\Delta t}, \ldots, \frac{t_{max}}{\Delta t} \right\}$$

$$\theta(n) = n\Delta\theta, n \in \{0, \ldots, (\pi/\Delta\theta) - 1\}$$

we have a total of $[(t_{max}-t_{min})(\pi-\Delta\theta)] / [(\alpha t)(\Delta\theta)]$ measurement points. To satisfy Equation 2 for generating the measurement points $m(t_k, \theta_n)$ in FIG. 6b the measurement must be taken at $k = 1,2,\ldots N_t$ and $n = 0,1,\ldots,(N_\theta - 1)$.

The increments $\Delta\theta, \Delta t$ are chosen in accordance with the degree of resolution desired in the reconstructed image. For example, higher resolution may be required in a brain study than in a liver study.

Figure 7A:
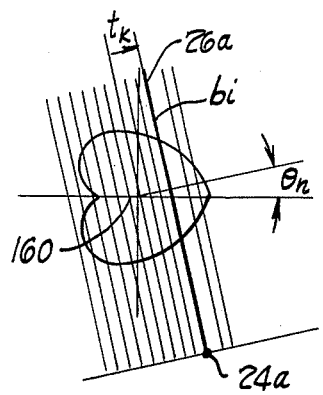
FIG. 7a is a functional representation of a conventional scanning technique which scans the measurement points of FIG. 6b.

One scanning technique which has been developed for generating the required data for reconstruction at the measurement points $m(t_k, \theta_n)$ is shown in FIG. 7a.

This technique is the rectilinear scanning technique described in the prior art section of this application and in the referred Cho publication. A radiation source 24a directs a beam of radiation, $b_t$, to radiation detector 26a. The source-detector pair 24a, 26a are rotatably and translatably held in spaced alignment. The pair 24a, 26a are translated at a selected orientation, $\theta$, about the origin 160 and a plurality of measurements are taken. At the completion of a translational scan, the source-detector pair 24a, 26a is rotated to a different angle $\theta$ and again is rectilinearly translated with measurements taken at the same translational values $t$.

The rectilinear scanning technique of FIG. 7a measures data at one of the measurement points $m(t_k,\theta_n)$ for each measurement during a translational scan. Therefore one translational scan generates one row of measurement points in FIG. 6b.

As earlier noted this rectilinear scanning technique requires acceleration, deceleration and direction reversals of the source-detector pair 24a, 26a at the end of each translational scan prior to rotation of the source-detector pair about the origin 160 to provide a new angle $\theta$. The acceleration, deceleration and direction reversal requirements of a source-detector pair of typically large mass limits the speed with which the necessary data can be collected. If 180 scans of the specimen are scheduled, a total of 179 direction reversals, accelerations, and decelerations must be accomplished for complete reconstruction. Not only is an unduly massive system requisite to accommodate these movements, but they are also unnecessarily time consuming.

Figure 7B:
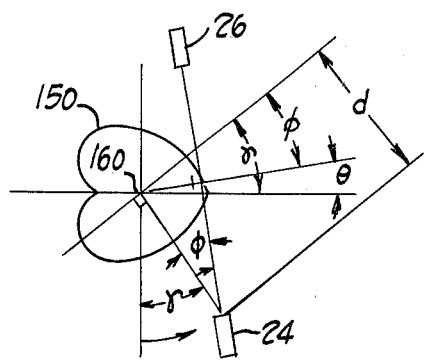
FIG. 7b is a functional representation of a compound axial scanning technique according to the invention which scans the measurement points of FIG. 6b.

FIG. 7b depicts an alternative scanning motion which provides the necessary orientations of the beam for taking measurements at the measurement points $m$ $(t_k,\theta_n)$ of FIG. 6b. FIG. 7b illustrates the compound axial scanning movement of the system 10 of FIG. 1 which minimizes the number of accelerations, decelerations and direction reversals required. The source 24-detector 26 pair is rotatable in the plane which contains the cross-sectional of the specimen 150. The pair 24, 26 rotates about the source axis 37 which is orthogonal to the cross-sectional plane and which is orbited about the origin 160. The axially moving pair 24, 26 provides a beam (or beams) in the cross-sectional plane which scans the specimen 150 in a plurality of orientations. Orbiting of the source-detector pair 24, 26 about the origin 160 (the system axis 49) defines the orbit angle $\gamma$. Rotation of the source-detector pair 24, 26 about the source axis 37 defines the rotation angle $\phi$.

As noted above the measurement points $m(t_k, \theta_n)$, depicted in FIG. 6b may be scanned using the compound angular scanning arrangement of FIG. 7b which may be implemented using the system 10 of FIG. 1. The measurement at the angle of rotation $\theta$ of clockwise rotation around the source pivot and the orbit angle of counter-clockwise rotation around the origin is identical to the measurement $m(t_k,\theta_n)$ at $t_k$ and $\theta_n$ in the original coordinate system with $t = d \sin \phi$ and $\theta = \gamma - \phi$, where $d$ is the distance from the source axis to the origin.

To acquire the same data in the new geometry, measurements must be made at $$\phi(k) = \sin^{-1} \frac{k \Delta t}{d} = \sin^{-1}\left(\frac{t_k}{d}\right) \qquad \text{EQN (4)}$$

and $$\gamma(k,n) = n \Delta\theta + \sin^{-1} \frac{k \Delta t}{d} = n \Delta\theta + \sin^{-1}\left(\frac{t_k}{d}\right) \qquad \text{EQN (5)}$$

For small values of the angle $\phi$, EQUATIONS (4) and (5) simplify to $$\phi(k) = \frac{k \Delta t}{d}; \gamma(k,n) = n\Delta\theta + \frac{\Delta t}{d} \qquad \text{EQN (6)}$$

A variety of compound angular scan motions are effective for either scanning the beam from the source 24 through the measurement points of FIG. 6b or sufficiently near the measurement points to provide the desired degree of accuracy in reconstruction. More specifically, the scanning paths, as will be described, may be designed to pass through the measurement points exactly, or they may be designed to pass proximate to the measurement points to an interpolation of the detected intensity to approximate a beam passing through the measurement point. If less accuracy is acceptable, the step of interpolation may even be eliminated. All such described paths will be referred to as passing through the measurement points.

Preferred scanning embodiments feature nonconcurrent, $\phi$ and $\gamma$ angular motions about the origin 160 and about the source axis 37 and are explained with respect to FIGS. 9a–9e and 10a–10b. Another scanning embodiment features concurrent scanning motions about the origin 160 and about the source axis 37 and is explained with respect to FIGS. 11a–11b. In both embodiments the scanning motions in the ($\phi,\gamma$) plane are controlled with respect to each other and to the angle $\theta$, and X-ray intensity measurements are taken to satisfy the angular relationships $\phi = \sin t/d; \gamma - \phi = \theta$.

Figure 8A:
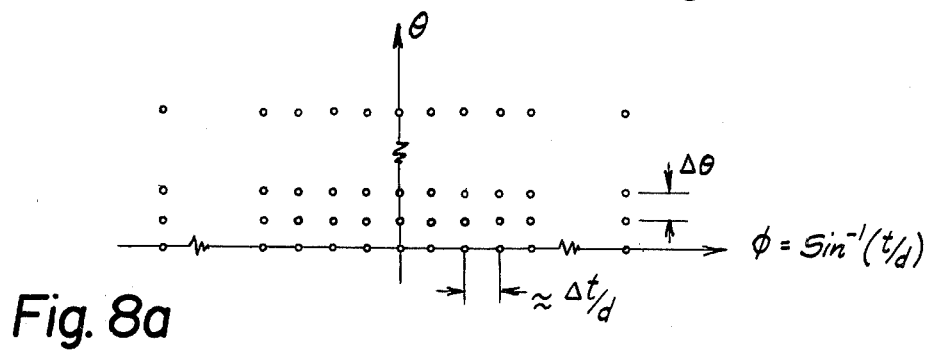
FIGS. 8a and 8b are graphs of the measurement points of FIG. 6b replotted in terms of compound angular motions $\phi$, $\gamma$.
Figure 8B:
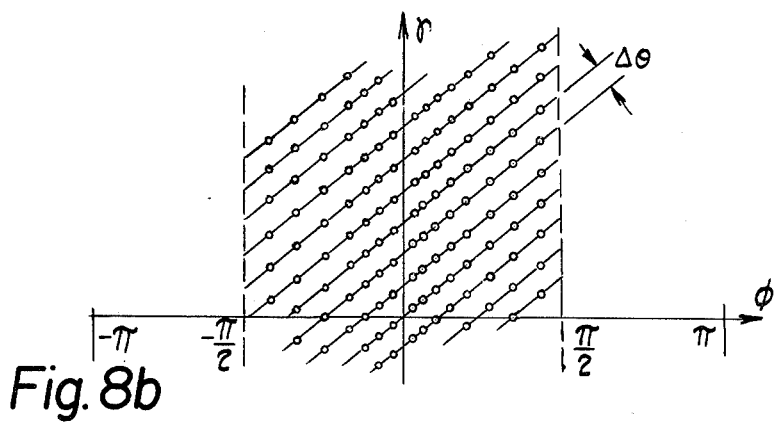

To facilitate understanding of the relationship between the scanning angles $\phi$, $\gamma$ to the measurement points, $m(t_k,\phi_n)$ in FIG. 6b, the measurement points are replotted as functions of ($\theta, \phi$) in FIG. 8a and as functions of ($\gamma,\phi$) in FIG. 8b. FIG. 8a assists in understanding a scanning motion mode which holds the angle $\theta$ constant, and FIG. 8b assists in understanding the compound angular scanning motion mode which does not hold the angular $\theta$ constant, As seen in FIG. 8a the measurement points $m$ ($t_k,\theta_n$) generally replot as an array of points in ($\theta,\phi$) having rows parallel to the $\phi$ axis. The points appear as substantially evenly spaced points in the $\phi$ direction for small values of the angle $\phi$. This is a reasonable approximation in the preferred scanning embodiment as the angle of rotation $\phi$ is generally limited to a relatively small range, such as ± 10°. More specifically, a typical X-ray source 100 provides a fan shaped beam spanning 20°. Because the angle $\phi$ is defined from the center of the array of detectors when used with a fan shaped beam the beam spans an angle $\phi$ of rotation of ± 10°. The approximation that $\sin \phi = \phi$ for small values of $\phi$ therefore holds. Because of the relationship between the angle of orbit $\gamma$, and the angle of rotation $\phi (\gamma = \phi + \theta)$ the plot in FIG. 8a may also represent a generalized plot of the measurement points $m$ ($t_k,\theta_n$) in the ($\theta,\gamma$) coordinate system.

The measurement points replot in the $\gamma$, $\phi$ plane as an array having rows at a 45° angle to the $\phi$ axis, as seen in FIG. 8b. The measurement points in the ($\gamma,\phi$) plane are evenly spaced in the $\gamma$ direction while they are shown nonuniformly spaced in the $\phi$ direction. This plot accommodates scans for the $\phi$ direction larger than 25°, which, it is understood, is not a preferred embodiment. For scans resulting in the angle $\phi$ of less than 20°, the points are generally uniformly spaced, as shown in FIG. 8a.

Figure 9D:
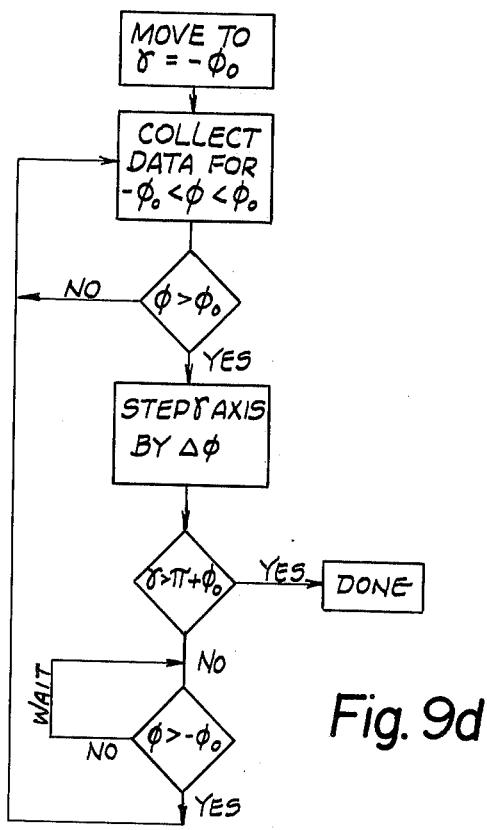
FIGS. 9a–e are diagrams which illustrate operation of the tomographic system of FIG. 1 to provide nonconcurrent compound axial scanning motions.
Figure 9C:
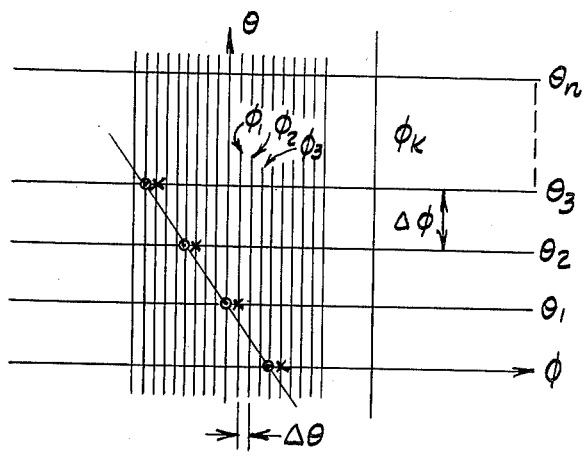
Figure 9A:
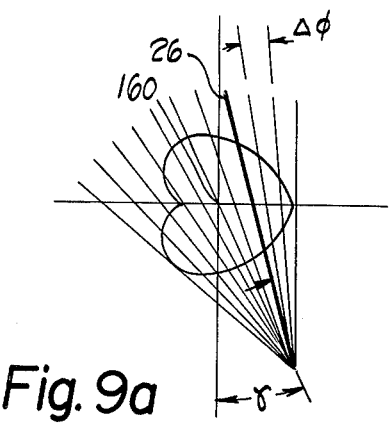

FIG. 9a depicts one embodiment of nonconcurrent angular motion of the source-detector pair 24, 26 about the source axis as the source axis orbits about the origin 160. At a selected value of the orbit angle $\gamma$, the source-detector pair 24, 26 is rotated about the orbiting system axis, and measurements are taken at angle of rotation $\phi_k = \gamma - \theta_n$. If an angle $\phi$ greater than 20° is desired, the system 10 in FIG. 1 is obviously modified to accommodate the motion. For example, the ledge portion 50 may be extended in the arc around the pivot shaft 48. A full 360° scan or a pair of 180° scans in the $\phi$ direction can thus be accommodated.

FIG. 9c shows the resulting points at which measurements are taken. The measurement line is a substantially straight line having a $(-\pi/4)$ slope. Increasing the angle of orbit $\gamma$ by $\Delta\phi$ will cause the line to intersect a new set of measurement points (shown by $x$'s) just to the right of the present set. Successive increments in the angle $\gamma$ results in measurements taken at all the required points at the angles $\phi_k = \sin^{-1}(t_k/d)$ and $\theta_n$ in the $(\phi,\theta)$ plane.

FIG. 9d represents a system operating diagram of the sequence in which the angles $\phi$, $\gamma$ are varied to generate the scanning path which traverses the desired measurement points. The system 10 is adjusted so that the angle $\gamma$ of orbit equals one extreme angle of rotation $\phi_o$, where the object under study is subtended by the angles $(-\phi_o,\phi_o)$. Data is then collected for $-\phi_o < \phi < \phi_o$ at the angles $\phi$ which satisfy the Equations 4, 5. After completion of this scan for a fixed angle, $\gamma$, the angle $\gamma$ is incremented by $(\phi_{k+1}) -\phi_k$, and the scan is repeated. This sequence of scanning continues until the angle of orbit equals the angle $\phi_o$ plus 180°. FIG. 9e shows a graph of the measurement points resulting from a plurality of 360° scanning paths, in the $\phi$ direction for selected angles of orbits $\gamma$.

Figure 9B:
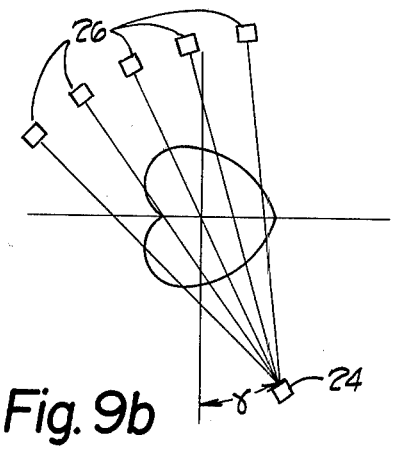
Figure 9E:
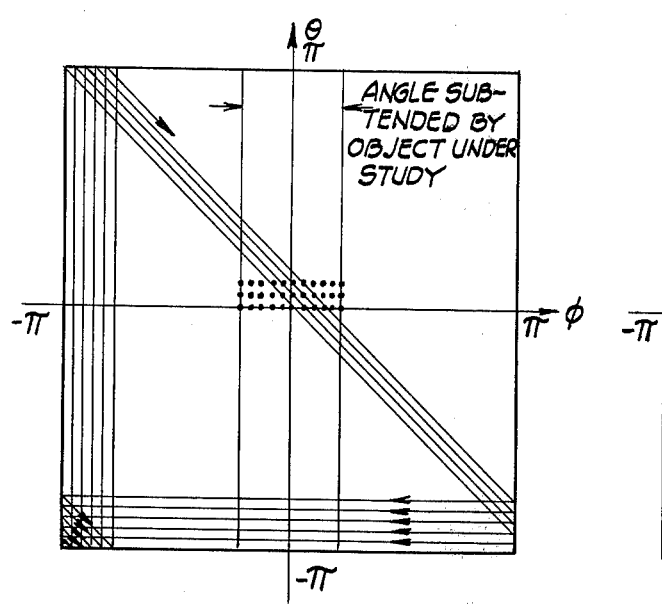

FIG. 9b illustrates the practical realization of the source-detector pair 24, 26 in FIG. 9a. A fan shaped beam is provided by the source 24 to generate a plurality of beams to a plurality of aligned detectors spaced in the plane. If a reconstructed image of low resolution is suitable, or if the fan shaped beam may be collimated sufficiently closely to enable a large number of beams, additional rotation of the source-detector pair in the $\phi$ direction about the source axis and additional orbital scanning is unnecessary. However, if greater resolution is required, or if a greater degree of collimation is required for preventing scattering of the beams, the multibeam providing source 24 is incrementally rotated about the source axis, and additional measurements are taken at the desired measurement points during another orbital scan.

Figure 10B:
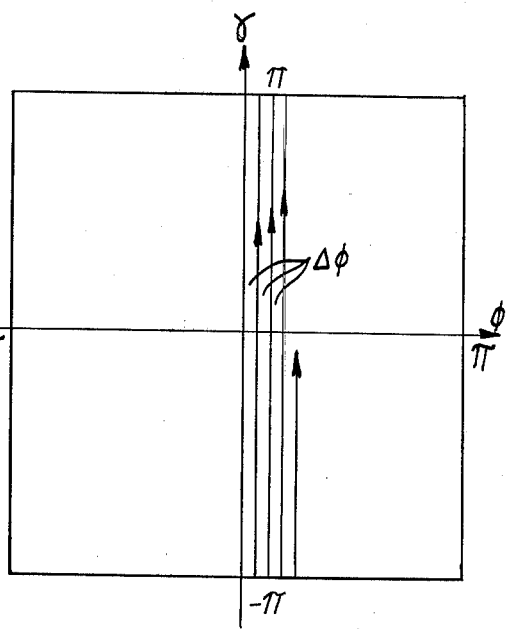
FIGS. 10a–10c are diagrams which represent a preferred operational embodiment of nonconcurrent compound axial scanning.
Figure 10A:
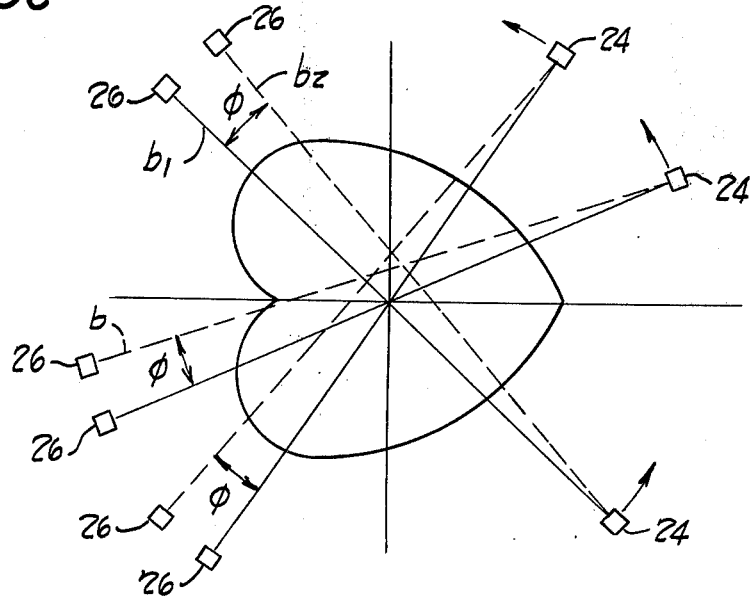
Figure 10C:
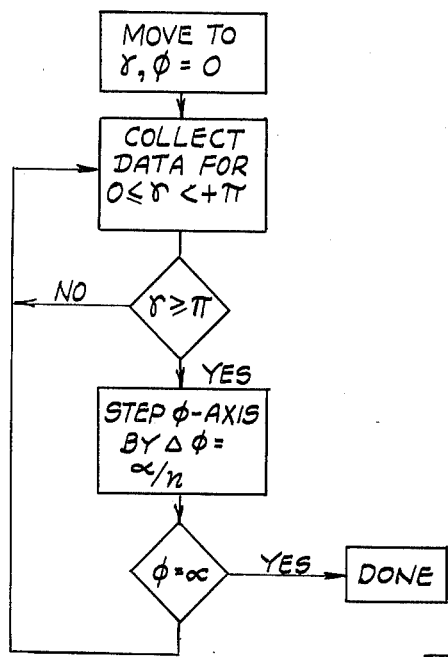

The preferred scanning embodiment for the system 10 which utilizes nonconcurrent $\phi$, $\gamma$ angular scanning motions is illustrated in FIGS. 10a–c. FIG. 10a illustrates two successive scans of the source-detector pair 24, 26, respectively, providing beams $b1$ and $b10b$ FIG. 10b represents a plot of the scan paths generated during a plurality of scans by the source-detector pair 24, 26 as plotted in the $(\theta, \gamma)$ plane. FIG. 10c represents a flow diagram illustrating a complete operating sequence for collecting data at the measurement points required for exact reconstruction.

In the preferred embodiment depicted in FIG. 10a, the source 24 provides a fan shaped beam spanning a twenty-degree angle of rotation $\phi$. It is understood that in the FIG. 10a the beams $b1$, $b2$ represent the center beam (or the center of the beam span if there are an even number of beams) of the plurality of beams, and accordingly, each is received by the center detector (or the assumed center detection if there are an even number of beams) of the array. The tube is oriented to provide the 20° beam through the cross-section, and a plurality of source collimators divides the fan beam into 20 collimated beams. Each beam is collimated to a width of 0.2 degrees. An aligned twenty-detector array is characterized by the angle $\alpha$ between adjacent detectors of 1° This combination allows measurements in a 20° arc every 1° in the angle $\phi$ of rotation without actual rotation of the pair 24, 26. For increased resolution, the pair 24, 26 is incrementally rotated between orbits through a total angle of 1°. Preferably measurements are taken at increments of the angle $\theta$ equal to 1° and at increments of the angle $\phi$ equal to 0.2°. For a sequence of 180° orbits, this schedule results in a matrix of 100 × 180 points spanning the cross-section of the patient. Increasing the number of incremental rotations in the angle $\phi$ increases the matrix density and thus provides increased resolution.

In operation, the patient under study is positioned on the stretcher 14 between the source-detector assemblies 24, 26. FIG. 10a shows a hypothetical cross-section of the patient substantially centered about the shaft 48 to provide an effective system axis passing through the patient about which the source-detector assemblies 24, 26 orbit. Table I below sets out the angles $\phi$, $\gamma$ at which measurements are desired for an array of 20 detectors, and an angle $\alpha$ of 1° between adjacent detectors, with the distance d between the origin and the source axis equal to 70 cm. The increment in the rotation angle $\phi$ is a submultiple of the angle $\alpha$; for example $\alpha/5 = .2°$. This schedule provides a 100 × 180 point matrix corresponding to $\Delta\theta$ equal to 1° and $\Delta t$ equal to .244 cm.

TABLE I

| $\phi$ | measure at $\gamma =$ |
|---|---|
| 0 | 0°, 1°, 2°, 3°, ...179° |
| .2 | 179.2°, 178.2° ...0.2° |
| .4 | 0.4, 1.4°, ...179.4° |
| .6 | 179.6°, 178.6° ...0.6° |
| .8 | 0.8, 1.8, ...179.8° |

For $\alpha = 1°$, $\alpha/n = .2°$, $d = 70$ cm.

Referring to the operating sequence depicted in FIG. 10c, the source detector pair 24, 26 is initially adjusted so that the angles $\gamma$, 100 equal 0. With the angle $\phi$ equal to O, the source detector pair is rotated through an arc of 180° in the $\gamma$ direction.

During the first scan measurements are taken at angles $N\alpha$, where $N = 0, 1, ..., 179$. Therefore, during the first scan measurements are taken every integer number of degrees between 0° and 179°. When the angle $\gamma$ reaches 180° the angle of rotation $\phi$ is incremented by an angle $\Delta\phi = \alpha/n$, where $n$ is any integer; choosing $n = 5$ as shown provides $\Delta\phi = 0.2$.

The source detector pair 24, 26 has rotated until the angle $\gamma = 180°$, it continues orbiting from $-180°$ to $0°$ about the specimen, or it reverses direction and orbits from 180° to 0°. Measurements are taken at the angles $\gamma = 179.2°, 178.°\ldots 0.2°$. The angle of rotation $\phi$ is then incremented by another 0.2°, and the process continues until the angle of rotation $\phi$ equals $\gamma$ or 1°. The scanning path in FIG. 10b is that of continuous rotation without direction reversal. This is the preferred scanning motion, as direction reversals are entirely eliminated. However, if the system 10 is operated to reverse motion in the $\gamma$ direction after every 180° scan, only 4 reversals are required for $n = 5$. This is the case illustrated in Table I.

Figure 11A:
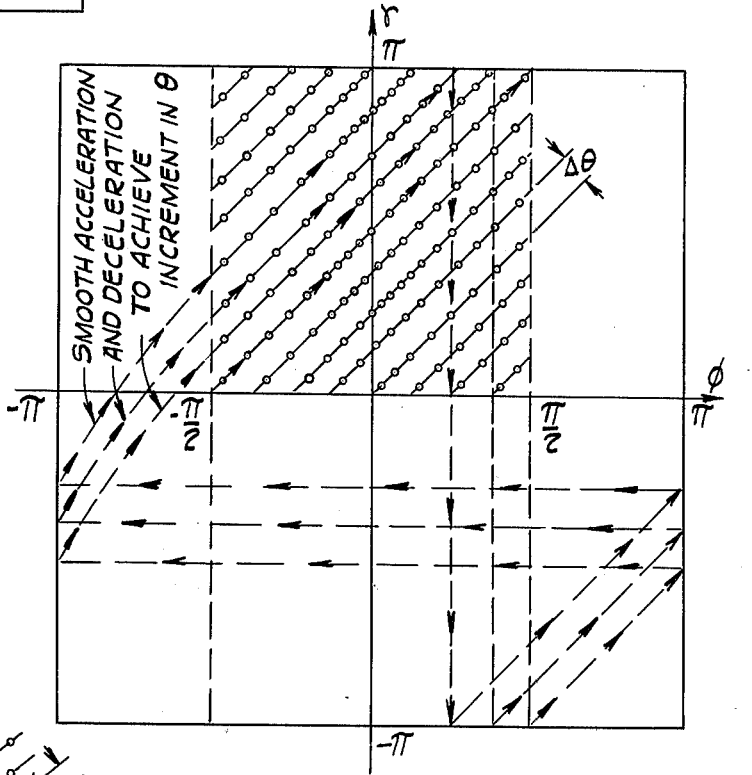
FIGS. 11a–b are diagrams which illustrate operation of the tomographic system of FIG. 1 to provide concurrent compound axial scanning motions.
Figure 11B:
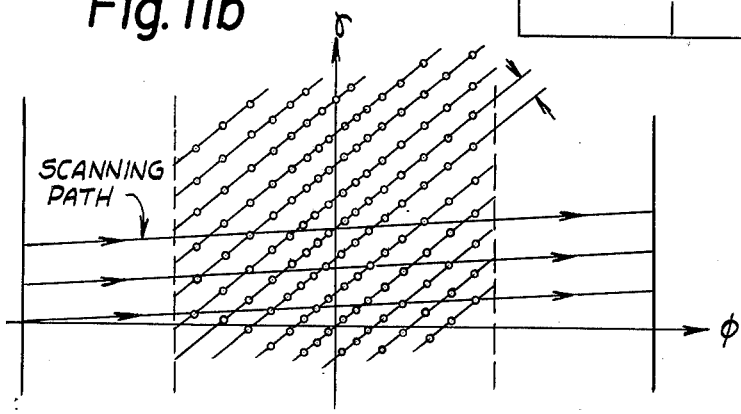

FIGS. 11a and 11b illustrate ($\gamma; \phi$) plots of the scanning path of the source-detector pair 24, 26 of FIG. 7b for concurrent $\gamma, \phi$ motions of the source-detector pair. The source detector pair is rotated about the arm 42 while the pair is orbited about the shaft 48. In FIGS. 11a and 11b, the measurement points $m(t_k, \theta)$ at which measurements are desired are replotted from FIG. 8b. In FIG. 11a motions of the source-detector pair 24, 26 are coordinated to maintain the angle $\theta$ a constant. The resulting scanning path is a set of lines having 45° slope which pass through the measurement points $(t_k \theta_n)$. Measurements are taken according to the Equations 4, 5 for exact reconstruction. To achieve the $\Delta\theta$ separation between scan paths, which enables coincidence with the measurement points, the source detector pair 24, 26 must be accelerated and decelerated. This acceleration and deceleration is easily obtained after the beam has scanned through the specimen and prior to the new scan because a reversal of the direction of the motions is not required.

FIG. 11b represents the scanning paths plotted against the measurement points $m (t_k, \theta_n)$ wherein the angle $\theta$ is not held constant during concurrent $\gamma, \phi$ motions. By choosing a relationship between the $\phi$ and $\gamma$ motions which control the value of the angle $\theta$ during the scan, the slope of the scanning path changes from 45°. Depending upon the selected slope, the scanning path may pass through multiple measurement points. If the path does not pass through the required measurement points, it will pass sufficiently near the measurement points so that an interpolation, such as a linear average, between data points by the processor 18 suffices for exact reconstruction.

While a single constructional embodiment of the apparatus of the invention has been illustrated and described herein in detail the invention is not to be considered limited to the precise construction shown. Other adaptations, modifications and uses of the invention may occur to those skilled in the art to which the invention relates, and it is intended to cover all such adaptations, modifications and uses which come within the scope of the appended claims.

What is claimed is:

1. Apparatus for repetitiously scanning an interior section of a body with a beam of radiation through coplanar points $[t(k), \theta(n)]$ about an origin in a plane passing through the body, comprising:
    a. a rotatable support assembly;
    b. rotatably mounted radiation source means supported by the assembly for orbit in said plane about an area including said origin, the source being adapted to transmit a beam of radiation along said plane and through a body under examination; said beam being of relatively small cross-sectional area compared to said body,
    c. radiation detector means connected to the assembly and aligned with said rotatably mounted source means for receiving said beam after it passes through such body; and,
    d. data collection means, including said radiation detector means, for measuring intensity values of said beam at values of an angle $\phi$ of rotation and at values of an angle $\gamma$ of orbit characterized substantially as $\phi = [(k\Delta t/d)]$ for small values of the angle $\phi$ and $\gamma = \phi + n \Delta \theta$, where $d$ represents the distance between the origin and the center of rotation of said rotatable radiation source means, and $k, n$ are integers.

2. Apparatus for repetitiously scanning an interior section of a body with a beam of radiation through substantially uniformly spaced coplanar points $[t(k), \theta(n)]$ about an origin in a plane containing the body section comprising:
    a. support means providing a source axis transverse to said plane and orbital around said origin;
    b. radiation source means rotatably coupled to said support means and orbital in said plane with said source axis around said origin, the source means being adapted to transmit a beam of radiation along said plane and through a body under investigation, said beam being of relatively small cross-sectional area compared to the body,
    c. radiation detector means coordinated with said radiation source means and disposed for receiving said beam after it passes through the body, and
    d. data collection means, including said radiation detector means, for measuring intensity values of said beam at values of angles $\phi, \gamma$ respectively about said source axis and about said system axis characterized substantially as $\phi = [(k\Delta t/d)]$ for small values of the angle $\phi$ and $\gamma = \phi + n \Delta\theta$ where $d$ represents the distance between the source and system axes, and $k$ and $n$ are integers.

3. Apparatus for repetitiously scanning an interior section of a body with a beam of radiation through substantially uniformly spaced coplanar points $[t(k), \theta(n)]$ about an origin in a plane containing the body section comprising:
    a. a support structure providing a source axis substantially orthogonal to said plane and oribital around an orbit axis through said origin;
    b. radiation source means rotatably coupled to said support structure and orbital with said source axis in said plane and around said origin, the source means being for transmitting a beam of radiation through a body positioned in part within said plane, said beam being of relatively small cross-sectional area having a diameter less than the distance between adjacent coplanar points;
    c. radiation detector means connected to the support structure and aligned with said radiation source means; the detector means being disposed for receiving said beam after it passes through such body, and,
    d. data collection means, including said radiation detector means, for measuring intensity values of said beam at values of angles $\phi, \gamma$ respectively about said source axis and about said system axis characterized substantially as $\phi = \sin^{-1} [(k\Delta\Delta t/d)]$ and $\gamma = \phi + n\Delta\theta$ where $d$ represents the distance between the source and system axes, and $k$ and $n$ are integers.

4. The scanning apparatus according to claim 3 wherein said support means includes a first motor for controllably orbiting said source axis around said system axis.

5. The scanning apparatus according to claim 4 wherein said support means includes a second motor for controllably rotating said source means around said source axis.

6. The scanning apparatus according to claim 3 wherein said source means includes:
   a. an X-ray tube for providing a fan shaped beam of radiation in said plane; and,
   b. collimator means for providing a plurality of beams from said fan shaped beam.

7. The scanning apparatus according to claim 6 wherein said radiation detector means includes:
   a. a collimator having plurality of collimator passages; and,
   b. a plurality of scintillators respectively aligned with said plurality of collimator passages.

8. Apparatus for repetitiously scanning an interior section of a body with a beam of radiation through substantially uniformly spaced coplanar points $[t(k), \theta(n)]$ about an origin in a plane containing the body section comprising:
   a. radiation source means for scanning a beam of radiation through the body, said beam being of relatively small cross-section compared to the body;
   b. radiation detector means disposed for receiving said beam after it passes through the body;
   c. rotatable support means for supporting and holding said source and said detector means in relative alignment to enable said detector means to receive said beam, said support means including:
      i. rotation means for controllably orbiting said source means in said plane through an angle $\gamma$ about said origin and for controlling rotating said source means through an angle $\phi$ about a source axis orthogonal to said plane and effectively passing through the radiation source means; and,
      ii. control means coupled to said rotation means for providing a controlled relationship between the orbital and rotational movements of said source means as the beam sweeps through the body during successive orbits; and,
   d. data collection means, including said radiation detector means, for measuring intensity values of said beam at angles $\phi$, $\gamma$ respectively about said source axis and about said origin characterized substantially as $\phi = \sin^{-1}[(k\Delta t/d)]$ and $\gamma = \phi + n\Delta\theta$ where $d$ represents the distance between the source axis and the origin, $k$ and $n$ are integers.

9. The scanning apparatus according to claim 8 wherein said control means includes a motor for accelerating and decelerating said source means between successive orbits.

10. Apparatus for repetitiously scanning an interior section of a body with a beam of radiation through substantially uniformly spaced coplanar points $[t(k), \theta(n)]$ about an origin in a plane containing the body section comprising:
    a. a radiation source for transmitting a beam of radiation through the body, said beam being relatively small cross-section compared to the body;
    b. radiation detector means disposed for receiving said beam after it passes through the body;
    c. rotatable support means for supporting and holding said source and said detector means in relative alignment to enable said detector means to receive said beam, said support means including:
       i. rotation means for concurrently rotating said source and said detector means in said plane through an angle $\gamma$ about said origin, and through an angle $\phi$ about a source axis effectively passing through the radiation source in a direction orthogonal to said plane; and
       ii. control means coupled to said rotation means for providing a linear relationship between the rotational movements of said source and detector means as the beam sweeps through the body; and,
    d. data collection means, including said radiation detector means, for measuring intensity values of said beam at angles $\phi$, $\gamma$ respectively about said source axis and about said origin characterized substantially as $\phi = \sin^{-1}[(k\Delta t/d)]$ and $\gamma = \phi + n\alpha\theta$ where $d$ represents the distance between the origin and the source axis, and $k$ and $n$ are integers.

11. Apparatus for repetitiously scanning an interior section of a body with a beam of radiation through substantially uniformly spaced coplanar points $[t(k), \theta(n)]$ about an origin in a plane containing the body section comprising:
    a. a radiation source-radiation detector pair disposed for transmitting a beam of radiation through the body;
    b. support means providing a source axis which orbits around the origin, said source-detector pair rotatably coupled to said orbiting source axis; and,
    c. data collection means, including said radiation detector, for measuring an intensity value of said beam at angles $\phi$, $\gamma$ about the source axis and about the origin respectively which are characterized substantially as $\phi = \sin^{-1}[(k\Delta t/d)]$ and $\gamma = \phi + n\Delta\theta$ where $d$ represents the distance between the source axis and the origin and $k$ and $n$ are integers.

12. A method of successively scanning an interior section of a body with an X-ray beam providing source for determining the coefficient of absorption at points $[t(k), \theta(n)]$ about an origin in a plane through the body comprising the steps of:
    a. scanning a beam of radiation from the source through the body to the detector;
    b. controllably orbiting said source in said plane through an angle $\gamma$ about a virtual system axis passing through said origin;
    c. controllably rotating said source in said plane through an angle $\phi$ about a virtual source axis;
    d. measuring the intensity of said beam at the angles $\phi$, $\gamma$ substantially characterized as $\phi = \sin^{-1}[(k\Delta t/d)]$ and $\gamma = \phi + n\Delta\theta$ where $d$ represents the distance between the origin and the source axis, and $k$ and $n$ are integers.

13. A method of successively scanning an interior section of a body with an X-ray for determining the coefficient of absorption at substantially uniformly spaced points $[t(k), \theta(n)]$ about an origin established in a plane through the body comprising the steps of:
    a. transmitting a beam of radiaion from an X-ray source through said body;
    b. detecting said beam with radiation detector means after it passes through the body;
    c. successively orbiting said source and said detector means in said plane around the origin through an angle $\gamma$ and controllably rotating said source and said detector means through an angle $\phi$ about a source axis effectively passing through and orbiting with said sorce; and, d. measuring the intensity of said beam at the angles $\phi$, $\gamma$ substantially characterized as $\phi = \sin^{-1}[(k\Delta t/d)]$ and $\gamma = \phi + n\Delta\theta$ where $d$ represents the distance between the source and system axis and $k$ and $n$ are integers.

14. The method of scanning according to claim 13 wherein said step of controllably rotating includes the step of accelerating and decelerating said source and said detector means between successive orbits.

* * * * *

UNITED STATES PATENT AND TRADEMARK OFFICE
CERTIFICATE OF CORRECTION

PATENT NO. : 3,983,399
DATED : September 28, 1976
INVENTOR(S) : Jerome R. Cox, Jr., et al.

It is certified that error appears in the above-identified patent and that said Letters Patent are hereby corrected as shown below:

In the Abstract, line 8, delete "and respectively"
In the Abstract in the equation; Col. 16, line 7; Col. 16, line 34; Col. 17, line 50; Col. 18, line 18, 36 and 53; and Col. 19, line 5, "[(k$\Delta$t/d)]" should be $-\left(\frac{k\Delta t}{d}\right)-$ Col. 2, line 42, after "Brain," insert -- " --
Col. 2, line 43, before "Radiology", delete " " "
Col. 8, line 18, "rotation" should be -- rotating --
Col. 8, line 27, after "102", "is" should be -- in --
Col. 10, line 15, after "iii.", "N" should be -- $N_\theta$ --

Col. 10, line 57, after "/", "[($\alpha$t)($\Delta\theta$)]" should be
-- [($\Delta$t)($\Delta\theta$)] --
Col. 12, line 21, after "points", "to" should be -- utilizing -
Col. 14, line 10, "detection" should be -- detector --
Col. 14, line 17, after "1°" insert -- . --

Col. 14, line 56, "100" should be -- $\phi$ --

Col. 15, line 2, "179.2°, 178.°...0.2°" should be -- -179.2°, -178.2°...0.2 --
Col. 15, line 4, "$\gamma$" should be -- $\alpha$ --
Col. 16, line 63, "[(k$\Delta\Delta$t/d)]" should be $-\left(\frac{k\Delta t}{d}\right)-$ Col. 18, line 18, "$\phi$ + n$\alpha\theta$" should be -- $\phi$ + n$\Delta\theta$ --
Col. 18, line 61, "radiaion" should be -- radiation --

Signed and Sealed this

Eighth Day of March 1977

[SEAL]

Attest:

RUTH C. MASON
*Attesting Officer*

C. MARSHALL DANN
*Commissioner of Patents and Trademarks*